United States Patent [19]

Eglington et al.

[11] 4,210,662
[45] Jul. 1, 1980

[54] SIDE CHAIN SULPHOXIDE METABOLITES

[75] Inventors: Alfred J. Eglington, Betchworth; Thomas T. Howarth, Cranleigh; David F. Corbett, Reigate, all of England

[73] Assignee: Beecham Group Limited, England

[21] Appl. No.: 800,347

[22] Filed: May 25, 1977

[30] Foreign Application Priority Data

Jun. 30, 1976 [GB] United Kingdom ............... 27201/76

[51] Int. Cl.² .................... C07D 487/04; A61K 34/40
[52] U.S. Cl. ............................... 424/274; 260/326.31; 424/114
[58] Field of Search ..................... 260/326.31; 424/274

[56] References Cited

U.S. PATENT DOCUMENTS

| | | | |
|---|---|---|---|
| 3,928,569 | 12/1975 | Umezawa et al. | 424/117 |
| 3,950,357 | 4/1976 | Kahan et al. | 260/326.31 |
| 4,000,129 | 12/1976 | Verwey | 260/239.1 |
| 4,022,773 | 5/1977 | Ishimaru | 260/239.1 |
| 4,123,547 | 10/1978 | Christensen et al. | 260/326.31 |
| 4,150,145 | 4/1979 | Christensen et al. | 260/326.31 |

OTHER PUBLICATIONS

Beecham Group Ltd.; Abstract of DT 2,513,855 (3/28/74).
Fieser et al., *Advanced Organic Chemistry*; p. 313 (1961).
Maeda et al., Heterocycles, vol. 9, p. 374 (1978).
Brown et al., Heterocycles, vol. 9, p. 231 (2 references).

*Primary Examiner*—Mary C. Lee
*Attorney, Agent, or Firm*—Jacobs & Jacobs

[57] ABSTRACT

Compounds of the formula

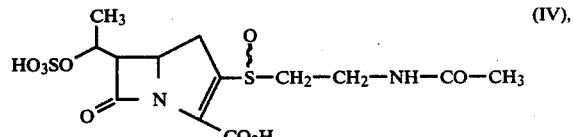

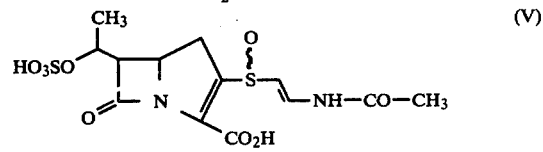

or

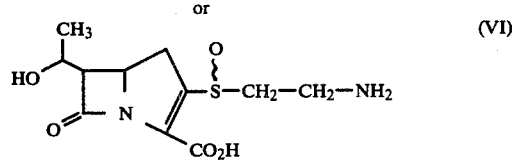

and salts thereof are useful both for their antibacterial activity and as synergists in combination with penicillins and cephalosporins.

12 Claims, No Drawings

SIDE CHAIN SULPHOXIDE METABOLITES

The present invention relates to antibacterial agents, to their perparation and to compositions containing them.

Belgian Pat. Nos. 839324 and 827332 relate to antibacterial and synergistic agents of the formulae (I) and (II) and U.S. Pat. No. 3,950,357 relates to the antibacterial agent of the formula (III):

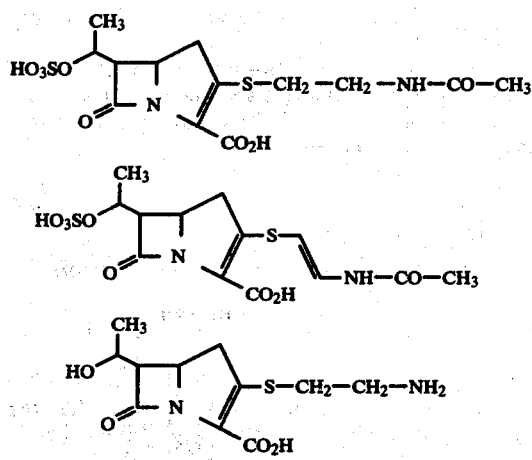

The compounds of the formulae (I) and (II) have been designated MM 17880 and MM 13902 and that of the formula (III) has been designated thienamycin.

It has now been discovered that oxidation of the sulphide atom in these molecules leads to the preparation of novel antibacterial and synergistic agents.

Accordingly the present invention provides the compounds of the formulae (IV), (V) and (VI):

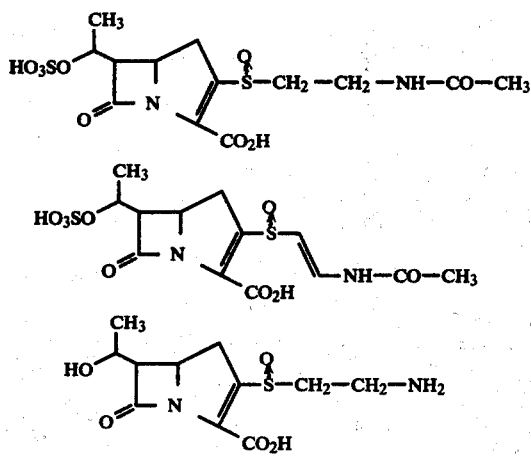

and salts thereof.

The compounds of this invention are in the form of a pair of stereoisomeric S-oxides.

Particularly suitable compounds of this invention are the salts of the compounds of the formula (VII):

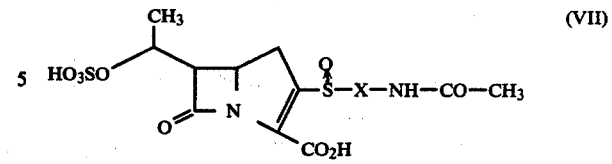

wherein X is a $-CH_2CH_2-$ or trans $-CH=CH-$ group.

Most suitably the compounds of the formulae (IV) and (V) are in the form of a mono- or di- salt of a pharmaceutically acceptable metal ion.

Perferably the compounds of the formulae (IV) and (V) are in the form of a di-alkali metal salt such as the di-sodium or di-potassium salt.

This invention also provides pharmaceutical compositions which comprise a compound of the formula (IV), (V) or (VI) or a salt thereof together with a pharmaceutically acceptable carrier.

The forms of the compositions of this invention will normally be similar to those described in the aforementioned Belgian or U.S. Patents.

Suitably the composition of this invention also comprises a penicillin or cephalosporin. Such synergistic compositions will normally contain from 1:10 to 10:1 parts (by weight) of penicillin or cephalosporin to parts (by weight) of a compound of the formulae (IV), (V) or (VI) or salt thereof.

The present invention also provides a process for the preparation of the compound of the formula (IV), (V) and (VI) and salts thereof which process comprises the S-oxidation of a corresponding compound of the formula (I), (II) or (III) or a salt thereof.

The process of this invention is normally carried out in aqueous solution at a non-extreme temperature. Suitable temperatures include the range 0°–30° C. and preferred temperatures are found within the range 10°–25° C.

Suitable oxidizing agents for use in this process are mild oxidizing agents such as organic per acids. Particularly suitable oxidizing agents include the optionally substituted perbenzoic acids, for example m-chloroperbenzoic acid.

Most suitably the oxidation reaction is carried out on a salt of a compound of the formulae (I) or (II), for example a di-basic salt such as the di-sodium salt.

The compounds of the formulae (IV) (V) or (VI) are normally isolated from an approximately neutral solution after oxidation is complete.

The following Examples illustrate the invention:

EXAMPLE 1

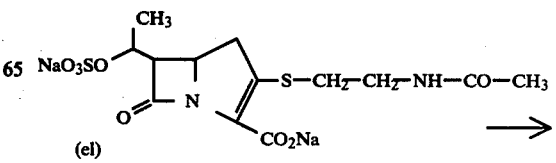

-continued

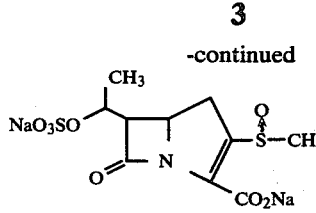

(e2)

The compound (e1) (54 mg) and m-chloroperbenzoic acid (23.4 mg) were stirred together in water (2 ml). After 10 minutes the m-chlorobenzoic acid that had formed was filtered off, the pH was adjusted to 7 by the addition of a small amount of dilute sodium bicarbonate solution and the water was then removed by evaporation on a rotary evaporator to yield the compound (e2) as a solid (60%).

$v_{max}$ (KBr) 1765, 1610 (broad), 1250 cm$^{-1}$; $\lambda_{max}$ (H$_2$O) 284 nm; $\delta$(D$_2$O) 1.5 (3H, d, J=6 Hz), 2.0 (3H, s), 2.8–4.0 (m) ppm.

EXAMPLE 2

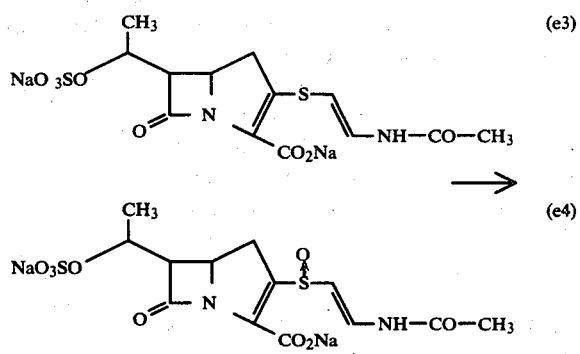

A solution of (e3) (0.3 g) in water (10 ml) was treated with solid m-chloroperbenzoic acid (0.17 g). A white precipitate of m-chlorobenzoic acid was rapidly formed, and after 10 minutes was filtered off. The remaining solution was neutralised to pH 7 with sodium bicarbonate and then chromatographed on QAE sephadex A 25 eluting with NaCl—phosphate buffer. The product was desalted on Amberlite XAD 4 using distilled water to elute, and then freeze-dried to afford a mixture of sulphoxides (1.2:1) (e4) as a white solid (0.176 g, 57%).

$v_{max}$ (KBr) 1765, 1690, 1620 br, 1210–1270 br cm$^{-1}$; $\lambda_{max}$ (H$_2$O) 287 and 237 nm; $\delta$(D$_2$O) 1.44 (3H, d, J=6 Hz), 2.02 (3H, s), 2.80–3.55 (2H, m), 3.85 (1H, m), 4.40 (1H, m), 4.8 (1H, m), 6.20 and 6.25 (total 1H, each d, J=14 Hz) and 7.45 (1H, d, J 14 Hz).

[The resonances at 6.20 and 6.25 indicate that the product is a mixture of 2 isomers and thus distingush it from the compounds disclosed in Belgian Pat. No. 827331].

What we claim is:

1. A compound of the formula

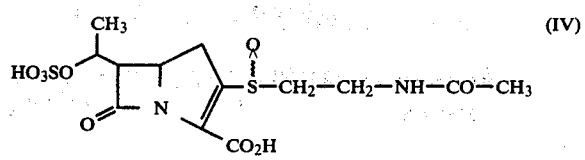

or a pharmaceutically acceptable salt thereof.

2. A pharmaceutically acceptable di-basic salt of a compound of claim 1.

3. A pharmaceutically acceptable di-alkali metal salt of a compound of claim 1.

4. The di-sodium salt of the compound of the formula (IV) of claim 1.

5. A pharmaceutical composition useful for treating bacterial infections in humans and animals which comprises an antibacterially effective amount of a compound for the formula

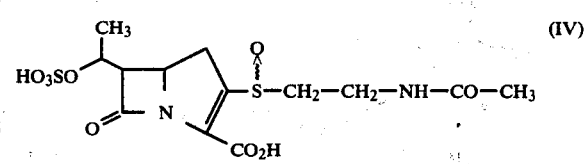

or a pharmaceutically acceptable salt thereof.

6. A composition according to claim 5 wherein the compound is in the form of a pharmaceutically acceptable di-basic salt.

7. A composition according to claim 6 wherein the compound is in the form of a pharmaceutically acceptable di-alkali metal salt.

8. A composition according to claim 5 wherein the compound is the di-sodium salt of the compound of the formula (IV).

9. A method of treating bacterial infections in humans and animals which comprises administering to a human or animal in need thereof an antibacterially effective amount of a compound of the formula

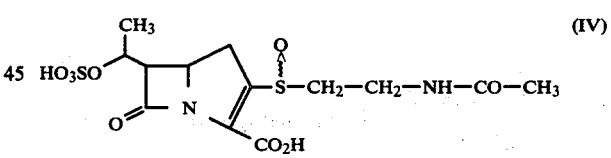

or a pharmaceutically acceptable salt thereof.

10. A method according to claim 9 wherein the compound is in the form of a pharmaceutically acceptable di-basic salt.

11. A method according to claim 9 wherein the compound is in the form of a pharmaceutically acceptable di-alkali metal salt.

12. A method according to claim 9 wherein the compound is the di-sodium salt of the compound of the formula (IV).

* * * * *